(12) United States Patent
Ina et al.

(10) Patent No.: US 6,346,651 B1
(45) Date of Patent: Feb. 12, 2002

(54) PROCESS AND APPARATUS FOR PRODUCING KETOISOPHORONE

(75) Inventors: Tomohide Ina; Noboru Kamei, both of Himeji; Hiroyuki Miura, Takasago, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/482,923

(22) Filed: Jan. 14, 2000

(51) Int. Cl.⁷ .......................... C07C 45/28; C07C 45/34
(52) U.S. Cl. ...................................... 568/344
(58) Field of Search ......................... 568/344

(56) References Cited

U.S. PATENT DOCUMENTS

| | | | |
|---|---|---|---|
| 3,931,327 A | * | 1/1976 | Strickler et al. |
| 4,046,813 A | * | 9/1977 | Brenner |
| 4,970,347 A | | 11/1990 | Bellut |
| 5,545,761 A | * | 8/1996 | Dawson et al. |

FOREIGN PATENT DOCUMENTS

| | | |
|---|---|---|
| EP | 0374416 A1 | 6/1990 |
| EP | 0808816 A1 | 11/1997 |
| EP | 0962440 A1 | 8/1999 |
| JP | A 49-81347 | 8/1974 |
| JP | A 50-93947 | 7/1975 |
| JP | A 51-125316 | 11/1976 |
| JP | B2 54-8650 | 4/1979 |
| JP | B2 55-30696 | 8/1980 |
| JP | A 61-191645 | 8/1986 |
| JP | A 10-53553 | 2/1998 |

OTHER PUBLICATIONS

Takahiro Hosokawa et al., Chemistry Letters, pp. 1081–1082, 1983.

* cited by examiner

Primary Examiner—Johann Richter
Assistant Examiner—Sikarl A. Witherspoon
(74) Attorney, Agent, or Firm—Birch, Stewart, Kolasch & Birch, LLP

(57) ABSTRACT

$\beta$-isophorone is formed by isomerizing $\alpha$-isophorone in the presence of an isomerizing catalyst (an aliphatic $C_{5-20}$ polycarboxylic acid) in an isomerizing-reaction unit 1. The $\beta$-isophorone thus formed is oxidized with oxygen in an inert solvent in the presence of an oxidizing catalyst (a complex salt of a transition metal and an N,N'-disalicylidenediamine) in an oxidizing-reaction unit 2, thereby forming ketoisophorone. After removing a low-boiling point component, which is an impurity (non-conjugated cyclic ketone), from the reaction mixture using a distilling unit 3, a high-boiling component (oxidizing catalyst) is separated in a distilling unit 4, and then ketoisophorone is separated from the solvent in the separation unit 5. Thereafter, the solvent containing 0 to 5,000 ppm (weight basis) of the impurities and substantially free from ketoisophorone is recycled to the oxidizing reaction through a recycling line 6. According to the present invention, the combination of the isomerizing reaction and the oxidizing reaction makes it possible to produce ketoisophorone from $\alpha$-isophorone while maintaining the activity of the oxydizing catalyst.

15 Claims, 1 Drawing Sheet

PROCESS AND APPARATUS FOR PRODUCING KETOISOPHORONE

FIELD OF THE INVENTION

The present invention relates to a process and an apparatus for producing ketoisophorone by oxidizing β-isophorone.

BACKGROUND OF THE INVENTION

Ketoisophorone (4-oxoisophorone) is an useful intermediate product in producing medicines, pesticides, perfumes, condiments, or polymers.

As a method for producing ketoisophorone from β-isophorone, Japanese Patent Application Laid-Open No. 125316 (JP-A-51-125316) discloses a method for producing an ethylenically unsaturated dicarboxylic acid by oxidizing β-ethylenically unsaturated ketone with molecular oxygen or a molecular oxygen-containing gas in the presence of an inorganic base or an organic base and a cobalt or manganese chelate. In this literature, as the solvent, there are enumerated aromatic hydrocarbons, chlorinated aliphatic hydrocarbons, lower aliphatic alcohols, ketones, carboxyamides, nitriles, amines, and ethers.

In Japanese Patent Application Laid-Open No. 53553/1998 (JP-A-10-53553) discloses a method for producing ketoisophorone by oxidizing β-isophorone with molecular oxygen in the presence of a manganese complex salt, an organic base, a specific substance having a catalytic action (e.g., organic acids having a pKa value of 2 to 7) and water. In this literature, the use of a ketone (e.g., acetone, methyl isobutyl ketone) or an ether as a solvent is also described.

According to these methods, however, when the reaction is repeated or the reaction is continuously carried out while circulating the solvent, an oxidizing catalyst is poisoned so that the activity is deteriorated, resulting in failure in maintaining high conversion and selectivity. Moreover, the use of some kind of base may considerably lower the conversion or selectivity of a substrate or causes the isomerization of from β-isophorone to α-isophorone. Particularly, when the concentration of β-isophorone in a reaction system is high (e.g., 20% by weight or higher), the yield of ketoisophorone is considerably reduced.

β-isophorone can be prepared by isomerizing α-isophorone in the presence of an isomerizing catalyst comprised of an acid. For example, in Japanese Patent Publication No. 8650/1979 (JP-B-54-8650) is disclosed a method for producing β-isophorone by the isomerization of α-isophorone in the presence of an isomerizing catalyst (an acid having a pKa value of 2 to 5) followed by distillation. In the literature, adipic acid is exemplified as the isomerizing catalyst and there is described that the continuous isomerization is usually carried out at atmospheric pressure though possible to conduct under reduced pressure.

Accordingly, there may be proposed a process of producing ketoisophorone from α-isophorone by combining the isomerizing reaction and oxidizing reaction. However, when the isomerizing reaction and the oxidizing reaction are employed in combination, the catalyst used in the oxidizing reaction is heavily poisoned, so that the catalytic activity is deteriorated. Therefore, the combination of the isomeriziing reaction and the oxidizing reaction results in difficulty in efficiently and continuously producing β-isophorone.

As a process for producing ketoisophorone from α-isophorone, in Japanese Patent Publication No. 30696/1980 (JP-B-55-30696), Japanese Patent Application Laid-Open No. 191645/1986 (JP-A-61-19164), and Japanese Patent Application Laid-Open No. 93947/1975 (JP-A-50-93947) are disclosed methods for producing 4-oxoisohporone by oxidizing α-ishophorone with oxygen in the presence of a catalyst. Japanese Patent Application Laid-Open No. 81347/1974 (JP-A-49-81347) discloses a method for producing 4-oxoisophorone by oxidizing α-isophorone with an alkaline metal chromic acid salt or a dichromate or a chromium trioxide. In the Chem. Lett. (1983), (7), 1081, there is disclosed a method for producing 4-oxoisophorone by oxidizing α-isophorone with t-butylhydroperoxide in the presence of a palladium catalyst. However, in these methods, since the selectivity to ketoisophorone is low, separation of the formed by-product (s) or a metal catalyst and purification of the object compound are made complicated. Moreover, these methods sometimes involve the use of a heavy metal compound such as chromium which requires special treatment, or a peroxide which is needed to be handled with care, which results in a decrease in working efficiency.

SUMMARY OF THE INVENTION

Thus, an object of the present invention is to provide a process and an apparatus for producing ketoisophorone while maintaining the activity of an oxidizing catalyst.

Another object of the present invention is to provide a process and an apparatus for continuously producing ketoisophorone from α-isophorone with high conversion and selectivity while maintaining the activity of an oxidizing catalyst high.

Still another object of the present invention is to provide a process and an apparatus for producing ketoisophorone capable of preventing an oxidizing catalyst from being poisoned even when an isomerization reaction and an oxidizing reaction are employed in combination.

The inventors of the present invention made intensive and extensive studies to achieve the aforementioned objects and found that, in the production process of ketoisophorone in which an inert solvent used in an oxidizing step is reused, a very small amount of impurities (e.g., ketones) present in the solvent poisons an oxidizing catalyst, so that the catalytic activity is considerably lowered. The present invention is based on the above findings.

Thus, the process of the present invention comprises a step for oxidizing β-isophorone in an inert solvent in the presence of an oxidizing catalyst to form ketoisophorone, a step for separating ketoisophorone and the solvent from the reaction mixture, and a step of recycling, at least, the separated solvent to the oxidizing step. In this process, the oxidizing catalyst comprises a complex salt of a transition metal and an N,N'-disalicylidenediamine. To prevent the deactivation of the oxidizing catalyst, the solvent from which a by-product [particularly, a compont with a low boiling point (impurities of low-boiling point] has been removed in the separation step is recycled to the oxidizing reaction; thereby producing ketoisophorone. The amount of the by-product(s) (impurities of low-boiling point) contained in the solvent to be recycled to the oxidizing step is 0 to 5,000 ppm (weight basis), and examples of the by-product (impurities) include non-conjugated cyclic ketones, and the like. Further, in a preferred embodiment, a solvent substantially free from ketoisophorone is recycled to the oxidizing step.

In the process of the present invention, ketoisophorone may be produced by combining an isomerization reaction and an oxidizing reaction. In this process, the β-isophorone is formed by isomerizing α-isophorone and the β-isophorone thus formed is subjected to the oxidizing step for oxidation.

The present invention also includes an apparatus for producing ketoisophorone which comprises: an oxidizing-reaction unit for forming ketoisophorone by oxidizing β-isophorone with oxygen, in the presence of an oxidizing catalyst, in an inert solvent; a separation unit for separating ketoisophorone, the solvent, and a low-boiling point component having a boiling point of 100 to 180° C. as a by-product from the reaction mixture; and a recycling line for recycling the solvent separated in the separation unit to the oxidizing-reaction unit.

DETAILED DESCRIPTION OF THE INVENTION

Figure 1:
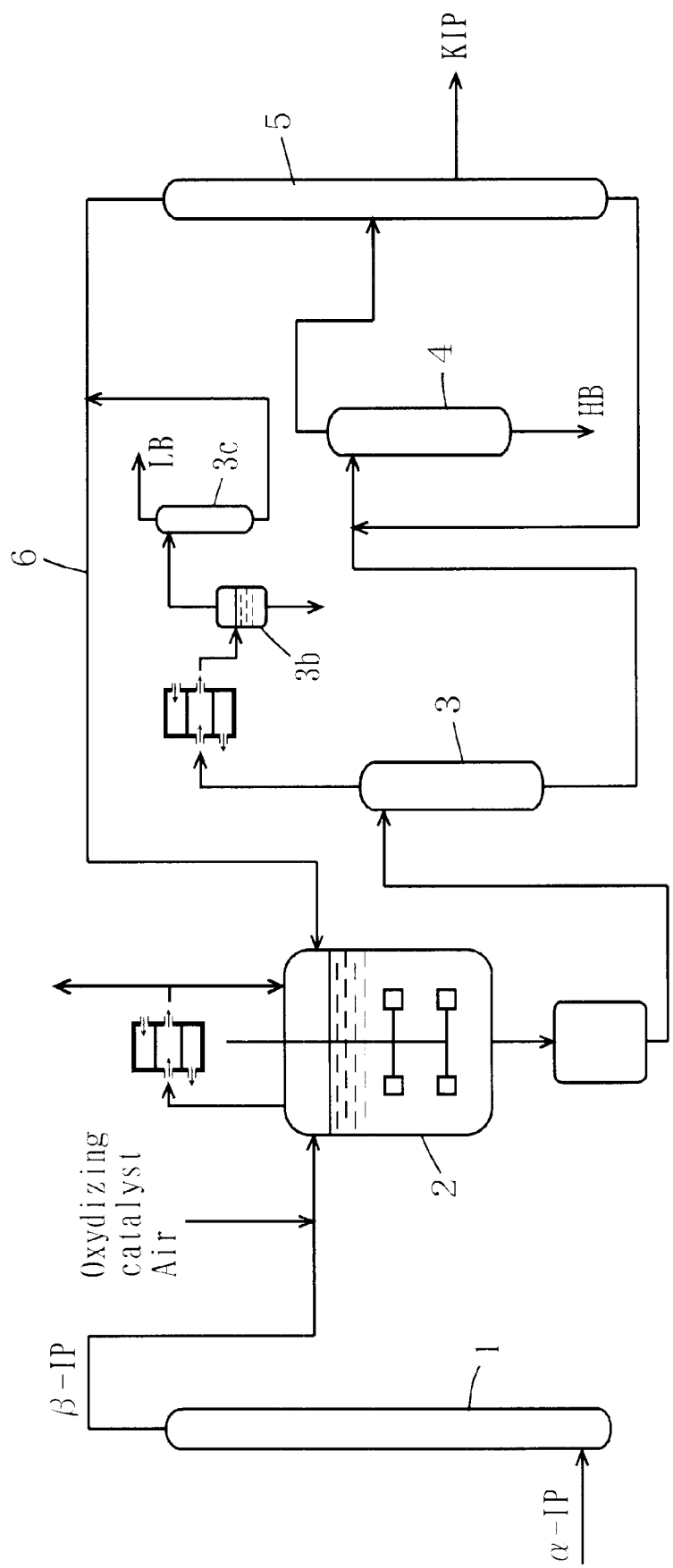
FIG. 1 is a flow chart for explaining the process and apparatus of the present invention.

Hereinafter, the present invention will be described in further detail, if needed, with reference to the chart attached.

FIG. 1 is a flow chart for explaining the process and apparatus of the present invention. In this embodiment, in the isomerizing step, β-isophorone is formed from α-isophorone in an isomerizing unit 1; in the oxidizing step with an oxidizing reaction unit 2, ketoisophorone is formed from β-isophorone prepared in the isomerizing step; and, in the separation step, ketoisophorone is produced by being separated and recovered successively in a separation unit. The separation unit is composed of: a distilling unit 3 for removing, among all by-products, a low-boiling point component from the reaction mixture formed in the oxidation reaction; a distilling unit 4 for removing a high-boiling point component from the reaction mixture; and a separation unit 5 for separating ketoisophorone and the solvent from each other. The solvent separated by the separation unit 5 is recycled to the oxidizing-reaction unit through the recycling line 6. Moreover, in this embodiment, the distilling unit 3 constituted of a distilling column is equipped with a separation system composed of a flash distiller 3b and a dephlegmeter 3c.

[Isomerizing step]

In the isomerizing step, α-isophorone is isomerized in the presence of an isomerizing catlyast to form β-isophorone.

As the isomerizing catalyst, at a pressure and a temperature for the isomerizing reaction, there can be used organic carboxylic acids having a boiling point not only higher than that of β-isophorone but also, for prevention of reverse isomerization, higher than that of α-isophorone, such as carboxylic acids having a boiling point of 250° C. or higher and derivatives thereof. Examples of an organic carboxylic acid are aliphatic carboxylic acids (e.g., $C_{12-24}$ higher aliphatic acids such hydroxystearate; aliphatic $C_{5-20}$ dicarboxylic acids such as glutaric acid, adipic acid, pimelic acid, suberic acid, azelaic acid, sebacic acid, and dodecanoic diacid), alicyclic carboxylic acids (e.g., alicyclic dicarboxylic acids such as 1,4-cyclohexanedicarboxylic acid, hexahydrophthalic acid, and himic acid), and aromatic carboxylic acids (e.g., aromatic polycarboxylic acids, aromatic monocarboxylic acids). These isomerizing catalysts can be used either independently or as a combination of two or more of these catalysts.

Preferred isomerizing catalysts are non-sublimate ones. Included among such isomerizing catalysts are aliphatic $C_{5-20}$polycarboxylic acids, and preferably aliphatic saturated $C_{6-12}$dicarboxylic acids (particularly, aliphatic $C_{6-10}$dicarboxylic acids such as adipic acid).

The amount of the isomerizing catalyst is, e.g., 1 to 15% by weight, preferably about 3 to 10% by weight, and particularly about 5 to 10% by weight, relative to α-isophorone.

Although it is possible to conduct the isomerizing reaction under atmospheric pressure, when the isomerizing reaction is carried out under atmospheric pressure, the reaction temperature becomes high and the isomerizing catalyst is thermal-cracked to generate a by-product. For example, when using an aliphatic dicarboxylic acid (e.g., adipic acid) as the isomerizing catalyst, the corresponding cyclic ketone (e.g., non-conjugated cyclic ketones such as cyclopentanone), water and carbonic acid gas is by-produced by thermal-cracking. Accordingly, as the amount of the isomerizing catalyst is gradually reduced, the amount of β-isophorone produced per unit time is reduced. Particularly, even when purifying β-isophorone by distillation, the by-product produced upon thermal-cracking (e.g., cyclopentanone) is mingled with the distilled β-isophorone, resulting in contamination.

Accordingly, in the isomerizing step, it is preferable that β-isophorone is produced, under reduced pressure and at a reaction temperature as low as possible, from α-isophorone with high efficiency. Particularly, for the separation and purification of ketoisophorone, it is effective to conduct the isomerization and the distillation or rectification of the isomerized product (vacuum distillation or rectification) under reduced pressure.

The isomerizing reaction is carried out at a temperature of, e.g., about 90 to 205° C. (e.g., 90 to 200° C.), preferably about 120° C. to 195° C., and more preferably about 140 to 190° C. The reaction pressure is usually, e.g., 10 to 600 Torr, preferably about 50 to 550 Torr, and more preferably about 100 to 500 Torr, depending on the reaction temperature. Incidentally, with proviso that the reaction temperature is not higher than the boiling point of the isomerizing catalyst and that the isomerization efficiency is kept and by-production of the by-product(s) is restrained, any combination of the reaction temperature and pressure can be employed. In the preferred process, the isomerization is conducted while inhibiting the decomposition of the isomerizing catalyst and restraining the production of a low-boiling point by-product resulting from the decomposition down to, on weight basis, about 750 ppm or lower (e.g., 0 to 700 ppm), and preferably about 600 ppm or lower (e.g., 0 to 500 ppm), thereby preventing the low-boiling point by-product from being mingled with β-isophorone.

The isomerizing reaction can be effected in a batch system, a semi-batch system, or a continuous system, though preferable to carry out by a continuous operation.

β-isophorone can be obtained by subjecting the reaction mixture to a conventional separation-purification means. Particularly, distillation or rectification (reaction distillation) using a distilling column (or a rectifying column) makes possible the industrially advantageous separation-purification of β-isophorone.

The distilling column may be either one of a packed column or a plate column. The number of plates of the distilling column is not particularly limited, but is usually 20 or more (e.g., 20 to 70 plates), and preferably about 25 to 50 plates. The distilling operation can be conducted, at an overhead temperature of about 120 to 185° C. (preferably, 150 to 185° C.) and a bottom temperature of about 200 to 250° C. (preferably, 210 to 230° C.), in accordance with a conventional method, e.g., by condensing steam from the overhead and then refluxing the condensate while extracting a portion of the condensate from the reaction system. The reflux ratio is, e.g., about 20 to 100, preferably about 30 to 80, and particularly about 40 to 80, and the residence time of the reaction mixture at the bottom may be, e.g., 30 minutes to 4 hours, and preferably about 1 to 3 hours. Moreover, for distillation, the number of distilling columns is not limited to one and a plurality of distilling columns can be used, if needed. The distillation can be performed in batches, yet continuous distillation is industrially advantageous.

Although the isomerizing reaction step and separation-purification step (distilling step) can be performed separately, in a preferred embodiment, α-isophorone is continuously fed to a reactor to be isomerized in the presence of an isomerizing catalyst, the isomerized reaction product is distilled, and the isomerizing reaction and separation-purification (distillation) are successively carried out in parallel operation relationship.

In the preferred embodiment, β-isophorone purified in the isomerizing step is then separated and purified successively in the separation-purifying step, and is subjected to the oxidizing step.

[Oxidizing step]

In the presence of an oxidizing catalyst, β-isophorone thus formed is oxidized in an inert solvent to form ketoisophorone.

The species of the oxidizing solvent is not particularly restricted, and a complex salt (or a complex) of a transition metal and N,N'-disalicylidenediamine or the like can be used. Such complex salt is useful informing ketoisophorone or a derivative thereof by oxidizing β-isophorone or a derivative thereof with molecular oxygen. As for the transition metal, the species or valence is not particularly limited and at least one transition metal selected from the elements of the Groups 3 to 12 of the Periodic Table of Elements can be used. The valence of the transition metal may be divalent to octavalnt, and is usually divalent, trivalalent, or tetravalent. Examples of the preferred transition metal are the Group 5 elements (e.g., vanadium V, niobium Nb), the Group 6 elements (e.g., chromium Cr), the Group 7 elements (e.g., manganese Mn, rhenium Re), the Group 8 elements (e.g., iron Fe, ruthenium Ru), the Group 9 elements (e.g., cobalt Co, Rhodium Rh), the Group 10 elements (e.g., nickel Ni, palladium Pd), and the Group 11 elements (e.g., copper Cu). The preferred metal is, for example, V, Mn, Fe, Co, Cu and the like, and Mn is particularly preferred. These transition metals can be used either singly or in combination.

The transition metal can form a complex shown by the following formula (1a) or (1b) together with a ligand N,N'-disalicylidenediamine (e.g., salene ligand).

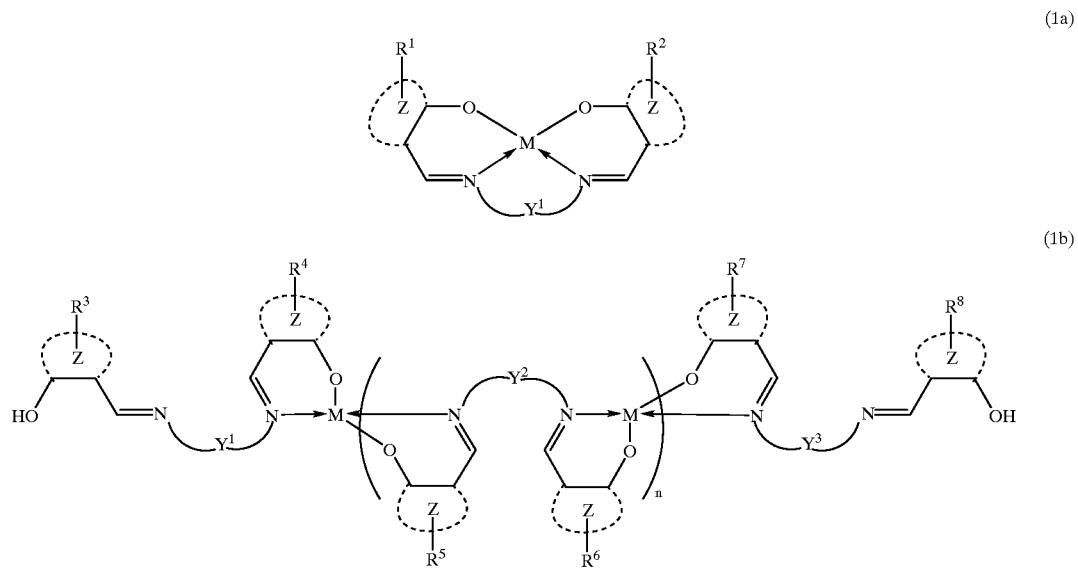

wherein M stands for the transition metal; $R^1, R^2, R^3, R^4, R^5, R^6, R^7$, and $R^8$ are the same or different from each other, each representing a hydrogen atom, a halogen atom, an alkyl group, a hydroxyl group, an alkoxyl group, a hydroxymethyl group; $Y^1, Y^2$, and $Y^3$ are the same or different from each other, each representing an alkylene group, a cycloalkylene group, or an arylene group; the ring Z stands for an aromatic ring; and n is an integer of 0 or 1 or larger.

As diamines corresponding to the above $Y^1, Y^2$, and $Y^3$, there may be exemplified aliphatic diamines such as straight- or branched chain $C_{2-10}$ alkylenediamines and $C_{2-10}$ alkylenediamines containing an imino group (NH group); alicyclic diamines such as a diaminocyclohexane; and $C_{6-12}$ aromatic diamines such as a diaminobenzene, a diaminonaphthalene, a biphenyldiamine; and derivatives thereof.

Examples of the preferred N,N'-disalicylidenediamine are N,N'-disalicylidene $C_{2-8}$alkylenediamines (preferably, N,N'-disalicylidene $C_{2-5}$alkylenediamine) such as N,N'-disalicylideneethylenediamine, N,N'-disalicylidenetrimethyienediamine, and N,N'-disalicylidene-4-aza-1,7-heptanediamine; and N,N'-disalicylidene $C_{6-12}$arylenediamines such as N,N'-disalicylidene-o-phenylenediamine, and N,N'-disalicylidene-2,2'-biphenylenediamine. Examples of the particularly preferred N,N'-disalicylidenediamine are N,N'-disalicylidene $C_{2-4}$alkylenediamines such as N,N'-disalicylideneethylenediamine and N,N'-disalicylidenetrimethylenediamine.

As the aromatic rings Z, there may be exemplified hydrocarbon rings (e.g., benzene, naphthalene) and heterocycles (e.g., nitrogen atom-containing heterocycles such as pyridine, pyrazine, pyrimidine, and quinoline; sulfur atom-containing heterocycles such as thiophene; and oxygen atom-containing heterocycles such as furan).

As to the substituents $R^1$ and $R^8$ of the aromatic rings Z, examples of the halogen atom are bromine, chlorine, and fluorine atoms, and examples of the alkyl group are $C_{1-6}$ alkyl groups such as methyl, ethyl, propyl, butyl, and t-butyl groups. Examples of the alkoxy group are $C_{1-6}$ alkoxy groups such as methoxy, ethoxy, propoxy, and butoxy groups. Each of the substituents $R^1$ to $R^8$ is usually a hydrogen atom, a $C_{1-4}$ alkyl group, or a hydroxymethyl group.

The complex may be amorphous, or crystalline like a composition represented by the formula (1b). In the formula (1b), n is an integer of 0 or 1, or higher (e.g., 1 to 5, particularly 1 or 2).

In the above complex represented by the formula (1b), n+1 mol of N,N'-disalicylidenediamine is coordinated with n mol of the transition metal, and thus the complex is structurally different from a complex represented by the formula (1a) in which 1 mol of N,N'-disalicylidenediamine is coordinated with 1 mol of the transition metal. Moreover, in contrast to the complex (1a) which is amorphous, the complex (1b) is crystalline and shows a clear melting point when subjected to thermal analysis by TC/TDA. The melting point of the complex (1b) is usually about 190 to 240° C. and particularly about 200 to 220° C. Moreover, the complex (1a) and (1b) can be distinguished from each other by whether an absorption peak derived from the hydroxyl group is observed in the infrared absorption spectrum or not.

The above complex can be obtained by coordinating an excess of an N,N'-disalicylidenediamine with a transition metal compound. As the transition metal compound, there may be exemplified organic acid salts (e.g., acetic acid salts), halides (e.g., manganese chloride), and inorganic acid salts. The proportion of the N,N'-disalicylidenediamine relative to the transition metal compound is about 0.5 to 5, preferably about 0.9 to 3, and particularly about 1 to 2 (molar ratio). The reaction of the transition metal compound with N,N'-disalicylidenediamine can be carried out in an inert solvent (e.g., an organic solvent such as an alcohol). The reaction can be effected by stirring the reaction mixture in an atmosphere of an inert gas, usually at a temperature of from 70° C. to the reflux temperature of the solvent.

The complex salt may be employed in combination with a nitrogen-containing compound to form a catalytic system. The nitrogen-containing compound contains at least one component selected from a cyclic base and a non-cyclic base. The preferred catalytic system can be constituted of (1) the combination of the complex salt or complex, and a cyclic base, or (2) the combination of the complex salt or complex, a cyclic base, and a non-cyclic base.

[Cyclic base]

As the cyclic base, there can be exemplified alicyclic and aromatic bases having at least one (preferably, two) nitrogen atom.

Alicyclic bases include bases in which at least one nitrogen atom constitutes a hetero atom of a ring, for example, 5 to 10-membered mono- and heterocyclic compounds such as pyrrolidine or derivatives thereof [N-substituted pyrrolidines (e.g., N-$C_{1-4}$ alkylpyrrolidines such as N-methylpyrrolidine), substituted pyrrolidines (e.g., 2- or 3-methylpyrrolidine, 2- or 3-aminopyrrolidine), or the like], piperidine or derivatives thereof [N-substituted piperidines (e.g., N-$C_{1-4}$alkylpiperidine such as N-methylpiperidine; piperylhydrazine), substituted piperidines (o-, m-, or p-aminopiperidine)]; alkylene imines or derivatives thereof [hexamethylene imine, N-substituted hexamethylene imines (e.g., N-methylhexamethylene imine)], and piperazine or derivatives thereof [N-$C_{1-4}$alkylpiperazines such as N-methylpiperazine; N,N'-di-$C_{1-4}$alkylpiperazines such as N,N'-dimethylpiperazine; 2-methylpiperazine]; and poly- and heterocyclic compounds such as azabicyclo $C_{7-12}$alkanes (e.g., quinuclidine, 1,4-diazabicyclo[2.2.2]octane (DABCO), 1,5-diazabicyclo[3.2.1]octane, 1,5-diazabicyclo[3.3.0]octane, 1,4-diazabicyclo[4.2.0]octane, 1,5-diazabicyclo[3.3.1]nonane, 1,5-diazabicyclo[5.3.0]decane), azatricyclo$C_{8-16}$alkanes (e.g., 1,5-diazacyclo[3.3.0.0$^{2,6}$]octane, hexamethylenetetramine), and derivatives thereof.

Among these alicyclic bases, those containing at least two (particularly, 2 to 6) nitrogen atoms are preferable. The preferred alicyclic base is, for example, a 6 to 8-membered mono- and heterocylcic compound (e.g., piperazine, N-substituted piperazines, amino-substituted piperazines); an azabicyclo$C_{7-10}$alkane (e.g., quinuclidine, DABCO, or derivatives thereof); or hexamethylenetetramine.

Included among the aromatic bases listed above are those having at least two nitrogen atoms in which at least one nitrogen atom constitutes a hetero atom of the ring. Example of such aromatic base are aromatic heterocyclic compounds in which at least one nitrogen atom constitutes a hetero atom of the ring (e.g., pyridine) substituted with a substituent having at leat a nitrogen atom (e.g., amino group, an N-substituted amino group) [N,N-di-substituted aminopyridines such as 2-, 3-, or 4-aminopyridine, 2-, 3-, or 4-mono- or di-alkylaminopyridines (e.g., di-$C_{1-4}$alkylaminopyridines such as dimethylaminopyridine), 2-, 3-, or 4-piperidinopyridine, and 4-pyrrolidinopyridine]; pyrazine or derivatives thereof (e.g., 2-methylpyrazine); phthalazine, quinazoline, quinoxaline, or derivatives thereof; phenanthroline or its derivatives (e.g., 1,10-phenanthroline); and 2,2-bipyridyl or its derivatives, with N,N-di-substituted aminopyridines, pyrazine, phenanthroline, or derivatives thereof particularly preferred.

In the above cyclic base, a nitrogen atom(s) other than the one constituting the ring is preferably a tertiary amine, and the nitrogen atom as a hetero atom constituting the ring may be substituted with a substituent other than hydrogen atom. The cyclic base can be used singly or in combination.

The proportion (molar ratio) of the cyclic base relative to the complex is about 20/1 to 500/1 and preferably about 30/1 to 300/1 (e.g., about 50/1 to 250/1).

[Non-cyclic base]

Non-cyclic bases constituting nitrogen-containing compounds include Schiff bases. Examples of the Schiff bases are compounds having an imino bond or an anil bond. Such Schiff bases include, for example, compounds shown by the following formulae (2a) to (2h) and compounds having a similar structure.

(2a)

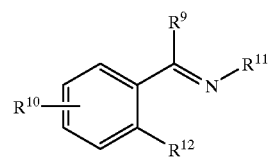

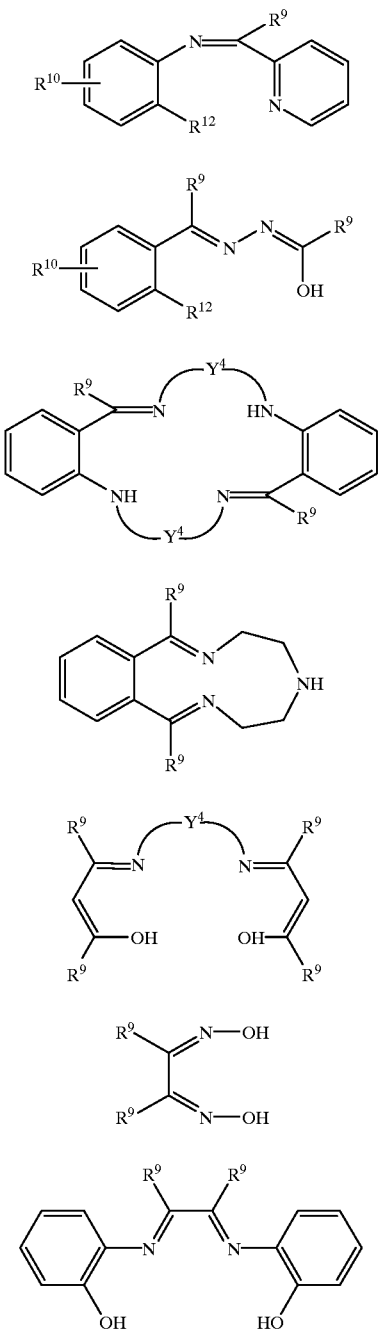

wherein $R^9$ and $R^{10}$ are the same or different, each representing a hydrogen atom, an alkyl group, an aryl group, or a cycloalkyl group; $R^{11}$ represents a hydroxyl group, an an amino group, an alkyl group, or an aryl group; $R^{12}$ represents a hydroxyl group, an amino group, an alkyl group, an aryl group, or a pyridyl group; and $Y^4$ represents an alkylene group or a cyclohexylene group. Exemplified as the groups designated by $R^9$ to $R^{11}$ and $Y^4$ are groups similar to those enumerated for $Y^1$ to $Y^3$.

Preferred nitrogen-containing groups include, for example, salicylaldoxime, bisacetylacetoneethylenediimine, dimethylglyoxime, diamine salicylaldimines that constitute the above-described complexes (e.g., N,N'-disalicylideneC$_{2-5}$alkylenediamines such as N,N'-disalicylideneethylenediamine, N,N'-disalicylidenetrimethylenediamine and N,N'-disalicylidene-4-aza-1,7-heptanediamine), compounds having an imino bond such as bisimine compounds, and compounds having an anil bond such as glyoxal bishydroxyanil. N,N-disalicylidenediamines constituting the above complexes include, for example, ligands for the complexes shown by the formulae (1a) and (1b).

The ratio (molar ratio) of the non-cyclic base to the complex is about 0.1/1 to 20/1, preferably about 0.5/1 to 15/1 (e.g., 0.5/1 to 10/1), and usually about 1/1 to 10/1.

In the oxidizing reaction, the amount of the oxidizing catalyst of the complex or the proportions of the constituents of the oxidizing catalytic system relative to 1 mole of β-isophorone are as follows: about $1\times10^{-5}$ to $1\times10^{-2}$ mol (preferably, $1\times10^{-4}$ to $1\times10^{-3}$ mol) of the complex; about $5\times10^{-2}$ to 1 mol (preferably, $1\times10^{-2}$ to 0.5 mole of the cyclic base; and $1\times10^{-5}$ to $1\times10^{-2}$ mole (preferably, $1\times10^{-3}$ to $5\times10^{-3}$ mole) of the non-cyclic base.

[Oxygen source]

Besides oxygen and oxygen-containing gases, as the oxygen source for the oxidizing reaction, a compound which generates oxygen can also be employed insofar as the compound is capable of supplying molecular oxygen. As the oxygen source, although high-purity oxygen gas can be used, it is preferred that an oxygen gas diluted with an inert gas, e.g., nitrogen, helium, argon, or carbon dioxide is supplied to the reaction system. Moreover, in the present invention, β-isophorone can be effectively oxidized even with air as a substitute oxygen source for oxygen.

The concentration of oxygen in the oxygen source is, e.g., 5 to 100% by volume, preferably about 5 to 50% by volume, and particularly about 7 to 30% by volume, and even if the concentration of oxygen is as low as 8 to 25% by volume, the oxidizing reaction proceeds effectively.

When supplying molecular oxygen to a reaction vessel or container, the reaction may be carried out in a closed system supplied with sufficient molecular oxygen, or may be conducted while allowing molecular oxygen to flow continuously. When allowing molecular oxygen to flow continuously, the flow rate is, for example, about 0.1 to 10 L/min and preferably about 0.5 to 5 L/min per unit volume (1L)

[Reaction solvent]

The oxidizing reaction is carried out in a solvent inert to the reaction. The species of the reaction solvent is not particularly restricted insofar as the solvent is separable from the reaction product. For separating the solvent from water generated in the oxidizing reaction or the nitrogen-containing compound (e.g., a cyclic base) in the catalytic system with a higher separation efficiency, it is preferred to employ a water-insoluble organic solvent. Examples of the water-insoluble organic solvent are aliphatic hydrocarbons such as hexane, heptane, and octane; aromatic hydrocarbons such as benzene, toluene, and xylene; alicyclic hydrocarbons such as cyclohexane; ketones (particularly, dialkyl ketones) such as methyl ethyl ketone and dibutyl ketones (e.g., diisobutyl ketone, di-t-butyl ketone); ethers such as diethyl ether, diisopropyl ether, dibutyl ether, tetrahydrofuran, dioxane, ethylene glycol monomethyl ether, ethylene glycol dimethyl ether, diethylene glycol monomethyl ether, and diethylene glycol dimethyl ether; halogenated hydrocarbons such as monochloroethane, dichloroethane, chloroform, carbon tetrachloride, and 1,2-dichloroethane; and esters such as methyl acetate, ethyl acetate, and butyl acetate. These solvents can be used either independently or in mixture. Preferred solvents include $C_{2-5}$alkyl-$C_{3-5}$alkyl ketones (particularly, dibutyl ketones).

In the oxidizing step, mingled impurities (e.g., impurities by-produced in the isomerizing reaction or the oxidizing reaction), where they are derived from is not critical, greatly lower the activity of the oxidizing catalyst. Therefore, preferred as the inert solvent in the oxidizing step is a solvent which is largely different in boiling point from the impurities, particularly a solvent having a boiling point higher than that of the above specific impurities (e.g., solvents having a boiling point higher than that of the above specific impurities by about 10 to 100° C., preferably by about 20 to 50° C.). The boiling point of the inert solvent is, e.g., 120 to 200° C., preferably about 130 to 180° C., and more preferably about 150 to 180° C.

The concentration of the substrate of the reaction system is not particularly limited and can be selected usually from the range of 5 to 70% by weight, and preferably from the range of about 15 to 60% by weight (e.g., 20 to 55% by weight).

The proportion of water contained in the reaction system at the initiation of the reaction can be selected from the range within which the activity of the oxidizing catalyst is not adversely affected, and is about 1% by weight or less (e.g., about 0.001 to 1% by weight) and preferably 0.5% by weight or less (e.g., about 0.001 to 0.5% by weight). More than 1% by weight of water facilitates the reaction in the initial stage. However, in some cases, the reaction does not proceed further or the selectivity to ketoisophorone is reduced. Further, the reaction system contains not only water present at the initiation of the reaction but also water produced by the reaction, and a finite amount of water is usually present in the present reaction system. Accordingly, the water contained in the oxidizing reaction system (particularly, water produced in the reaction) can be separated in the separating step which will be described later and is removed from the reaction system. The amount of water to be removed out of the reaction system is at least 30% by weight, preferably at least 50% by weight, and more preferably at least about 80% by weight, relative to the total amount of water generated.

The reaction temperature can be selected according to the reaction rate, selectivity, and a solvent to be used. To eliminate the risk of explosions, it is desirable that the reaction is conducted at a temperature lower than the flash point of the reaction solvent. For example, in the case of diisobutyl ketone (flash point: about 49° C.) employed as the solvent, the reaction can be effected at a temperature within the range of about 35 to 45° C. Moreover, the reaction is usually carried out at atmospheric pressure, though possible to conduct at either atmospheric pressure or applied pressure [to about 150 atm ($152 \times 10^5$ Pa)]. The reaction time (residence time in a flow reaction) is not particularly restricted, and usually about 0.5 to 30 hours (e.g., 1 to 10 hours). The reaction is usually effected in a batch system, though possible to conduct in any system, such as a batch system, a semi-batch system, and a continuous system.

In the oxidizing step, there can be used a gas-liquid agitation-type oxidation reactor, and the amount of supplied oxygen and the conditions for stirring may sometimes affect the reaction selectivity. The preferred reactor is a reactor of high stirring efficiency, and such reactor may be equipped with a plurality of tiers (e.g., two tiers) of disc turbine rotor blades (e.g., 4 to 8 blades), and/or a plurality of buffle plates (e.g., 2 to 6 buffle plates). Further, oxygen may be supplied to the reaction system by being squirted into the system in bubbles by a sparger. The stirring energy of the reactor per unit volume can be selected from the range of about 0.5 to 5 kw/m$^3$ (preferably, 0.7 to 2.5 kw/m$^3$).

The starting materials can be added to the reaction system in any order, and there is no particular restriction on the order. However, for preventing the isomerization to α-isophorone, it is preferred that β-isophorone is supplied last to the reactor, that is, after a component(s) (e.g., an oxidizing catalyst) other than β-isophorone has been fed to the reactor. Further, for inhibiting the generation of heat, β-isophorone may be continuously or intermittently supplied to the reaction system by dropping.

[Separating step and recycling step]

In the separating step, ketoisophorone, the oxidizing catalyst, the solvent, and the low-boiling point impurity (or impurities) are separated from the reaction mixture resulted from the oxidizing reaction and, in the recycling step, the separated solvent is circulated back to the oxidizing step.

[Removal of the low-boiling point component]

In the separating step, it is important to remove the reaction by-product, particularly, the low-boiling point component(s) (impurities) contained in the reaction product. If the separated solvent is contaminated with the low-boiling point component(s) (impurities), even in a small amount, the solvent circulated back to the oxidizing step considerably poisons the oxidizing catalyst. As a result, the catalytic activity is considerably lowered, leading to failure in continuously forming ketoisophorone. Accordingly, the separating step requires that the solvent is highly separated and removed such as to be substantially free from impurities.

Although the species of the low-boiling point component (s) (impurities) is not particularly limited insofar as it is a component which poisons the oxidizing catalyst, the low-boiling point component may be a component which is by-produced in the isomerizing step (particularly, the decomposed of the isomerizing catalyst), such as a cyclic ketone, a hydroxyl group-containing compound (e.g., alcohols such as cyclic alcohols) and a carboxyl group-containing compound (e.g., carboxylic acids such as cyclic carboxylic acids). Particularly, cyclic ketones (among others, non-conjugated cyclic ketones) seem to largely deteriorate the activity of the oxidizing catalyst. Such cyclic ketones include, e.g., $C_{4-20}$cycloalkanones that are correspondingly by-produced from aliphatic dicarboxyic acids such as adipic acid. The boiling point of the low-boiling point component(s) (impurities) is usually about 100 to 180° C. (e.g., 100 to 160° C.), and particularly about 120 to 140° C.

For maintaining the activity of the oxidizing catalyst, in the separating step, it is preferred that the solvent to be recycled back to the oxidizing step is separated and purified such that the content of the impurities (the low-boiling point impurities) is about 0 to 5,000 ppm, preferably 0 to 3,000 ppm, and preferably about 0 to 2,000 ppm (e.g., about 0 to 1,000 ppm).

The low-boiling point component(s) (impurities) can be removed by a conventional separating means, and condensation, distillation, extraction, or a combination means thereof may for example be adopted. Usually, the removal is carried out using a distilling column (or a rectifying column). The distilling column may be either a packed column or a plate column.

The low-boiling point component (impurities) may be removed in a single separating step, or through a combination of steps. In FIG. 1, when eliminating the low-boiling point component with a distilling column 3 in a single separating step, the number of plates of the distilling column is not particularly limited, and may for example be about 5 to 50 plates, preferably about 5 to 30 plates. The distilling operation can be performed at an overhead temperature of about 30 to 80° C. (preferably, 30 to 70° C.), a bottom temperature of about 80 to 150° C. (preferably, 100 to 130°

C.) and at a pressure of about 50 to 200 mmHg (preferably, 70 to 150 mmHg). The low-boiling point component can be removed in a conventional manner, for example, by refluxing the solvent at a suitable reflux ratio (e.g., about 100 to 700, preferably about 200 to 600).

A combination of separating steps is advantageous in separating water or the solvent from the low-boiling point component while separating the low-boiling point component from the reaction mixture. For example, as shown in FIG. 1, the low-boiling point component is effectively removed by a combination of the distillation (distilling column 3) for separating the low-boiling point component from the high-boiling point component, the flash distillation (flash distillation unit 3b) of the separated low-boiling point component and, if necessary, the dephlegmation (dephlegmator 3c) of the flash-distilled low-boiling point component, and the inert reaction solvent contained in the distillate is separated and effectively utilized.

For distilling the low-boiling point component from the overhead of the distilling column more, the low-boiling point component may be subjected to the flash distilling unit 3b. As the flash distilling unit 3b, a conventional one, such as WFE (wiped film evaporator) and FFE (falling film evaporation), can be used. The temperature and pressure for the flash distillation can suitably be selected, and the flash distillation is performed, for example, at a temperature of about 20 to 70° C. (preferably about 30 to 50° C.) and a pressure of about 10 to 150 mmHg (preferably, 30 to 100 mmHg). Usually, in the distilling operation, water contained in the reaction system is distilled off together with the low-boiling point component. In this case, water is separated from the bottom of the flash distilling unit 3b.

Furthermore, the low-boiling point component (impurities) contained in the component distilled off from the overhead of the flash distilling unit 3b can be almost completely removed by dephlegmating the low-boiling component using a conventional dephlegmator 3c. The dephlegmation can be performed, e.g., at a temperature of 20 to 70° C. (preferably, about 30 to 50° C.) and a pressure of about 10 to 100 mmHg (preferably, about 20 to 80 mmHg).

Incidentally, a small amount of the reaction solvent is usually present in the low-boiling point distillate containing the low-boiling point component. Therefore, the low-boiling point distillate may be subjected to another distillation or rectification operation to separate and recover the reaction solvent, followed by the recycling of the solvent back to the oxidizing step. In this case, the reaction solvent is recovered from the bottom of the dephlegmator 3c and merged into the recycling line 6.

From the bottom of the distilling column 3 is distilled off the reaction mixture from which the low-boiling point component has been removed but still containing the oxidizing catalyst as a high-boiling point component. The distillate is then subjected to the second separating step for separating the oxidizing catalyst. The separation can be carried out in a conventional manner, for example, by using a distilling column 4 (particularly, a flash distilling unit). The flash distillation is performed at a temperature of about 80 to 150° C. (preferably, 90 to 120° C.) and a pressure of about 10 to 100 mmHg (preferably, 20 to 80 mmHg), depending on the species of the catalytic component. The oxidizing catalyst can be recovered from the bottom of the column through such distilling operation, and a distillate mainly comprised of ketoisophorone and the solvent is distilled off from the overhead of the distilling column.

The oxidizing catalyst recovered from the bottom of the second distilling column 4 is recycled to the oxidizing step directly or, if necessary, after being reproduced for reuse.

[Recovery of ketoisophorone and recycling of the solvent]

Ketoisophorone and the inert solvent are removed from the reaction product distilled off from the overhead of the second distilling column, and the resultant reaction product is then subjected to the recovering step for recovering ketoisophorone and to the recycling step for recycling the inert solvent. Separation of ketoisophorone from the inert solvent and the recovery of ketoisophorone can be effected using a conventional separation-purification means, such as a distilling column 5 (recovering column).

The number of plates of the distilling column (recovering column) may be about 10 to 80, and preferably about 20 to 50. The distilling operation may be performed at an overhead temperature of about 30 to 100° C. (preferably, 50 to 80° C.), a bottom temperature of about 120 to 200° C. (preferably, 150 to 180° C.), and a pressure of 5 to 100 mmHg (preferably, 10 to 50 mmHg), and the reaction product may be distilled in a conventional manner, for example, by refluxing at a suitable reflux ratio (e.g., about 1 to 50, preferably about 1 to 25).

Incidentally, the inert solvent having a boiling point lower than that of ketoisophorone is usually distilled off from the overhead, though it does not matter if ketoisophorone is distilled off, and this depends on the boiling points of ketoisophorone and the inert solvent. It is preferred that ketoisophorone is recovered at a plate of a certain height of the distilling column (recovering column) (e.g., a plate at a height of 40 to 80% from the bottom).

The solvent separated from ketoisophorone is recycled to the oxidizing reactor through the recycling line. At that time, if ketoisophorone is mingled with the purified solvent, the oxidizing catalyst is poisoned. Therefore, it is preferred that the solvent is highly separated and purified by the distilling column such that the distilled inert solvent (solvent to be recycled to the oxidizing step) contains substantially no ketoisophorone. Incidentally, the phrase "contains substantially no ketoisophorone" means that, when determined by a analyzing means (gas chromatography), the content of ketoisophorone is equal to the detection limit value or lower.

Incidentally, for distillation of the low-boiling point component, high-boiling point component, ketoisophorone, or solvent, the number of distilling column is not limited to one, and a plurality of distilling columns can be used, if necessary. The distillation may be performed batchwise, yet continuous distillation is industrially advantageous.

Furthermore, in the separating step, insofar as the low-boiling point component, the high-boiling point component (oxidizing catalyst), the solvent, and ketoisophorone are individually separable from the oxidation reaction mixture, the components can be separated from the reaction mixture in any order. For example, inverse to the above-described process and the apparatus, the low-boiling point component (impurities) may be removed after the high-boiling point component (oxidizing catalyst) has been separated thereby to recover the oxidizing catalyst. Furthermore, the nitrogen-containing compound constituting the oxidizing catalytic system may be separated at a suitable stage, for example, at the separating step of low-boiling point component, the separating step of the high-boiling point component, the separating step of ketoisophorone from the solvent, or at a later stage, and, if necessary, recycled to the oxidizing step.

The separation or removal of the high-boiling point component is not necessarily required, and the reaction mixture from which the low-boiling point component has been removed may be subjected to the separating step for separating ketoisophorone from the solvent. Furthermore, the isomerizing step is not necessarily required, and the low-boiling point component formed in the oxidizing reaction may be removed from the reaction mixture and the solvent substantially free from ketoisophorone may be recycled to the oxidizing reaction.

According to the present invention, since the solvent from which the low-boiling point component conducive to deterioration in the activity of the oxidizing catalyst is recycled to the oxidizing step, ketoisophorone can be produced while maintaining the activity of the oxidizing catalyst. Particularly, even when the isomerizing step and the oxidizing step are combined, ketoisophorone can be continuously produced from α-isophorone with high conversion and high selectivity while maintaining the activity of the oxidizing catalyst high, and the oxidizing catalyst is prevented from being poisoned.

EXAMPLES

Hereinafter, the present invention will be described in further detail and should by no means be construed as defining the scope of the present invention.

Example 1

Using the apparatus shown in FIG. 1, ketoisophorone was produced through the isomerizing reaction and the oxidizing reaction in the following manner.

(1) Isomerizing step

α-isophorone (α-IP) and 7% by weight of adipic acid relative to the amount of α-isophorone were fed to the bottom of the oldershow distilling column (30 plates, 50 mmφ) equipped with a vacuum jacket, and the bottom was heated to start the mixture refluxing. Thereafter, β-isophorone (β-IP) was obtained in the form of a distillate at a distilling rate of 30 g/hr while supplying α-IP to the bottom of the distilling column at a supply rate of 30 g/hr. The distilling column was manipulated at an atmospheric pressure and a reflux ratio of 63. Moreover, the residence time of α-IP at the bottom was 2 hours, the temperature of the bottom was 220° C., and the temperature of the distillate was 183° C.

(2) Oxidizing step 0.92 g of manganese salene complex and 68 g of diazabicyclooctane (DABCO) were fed to a glass atmospheric oxidizing reactor (volume: 10 L), and successively 1036.5 g of β-IP and 3420.6 g of diisobutylketone (DIBK) were added thereto. The mixture was reacted by stirring the mixture with a disk turbine blade (50 mmφ) at a rotating speed of 300 rpm while allowing air to flow at 40° C. After being reacted for 5 hours, the reaction mixture was analyzed by gas chromatography, and it was found that 996 g of ketoisophorone (KIP) was formed with a conversion of 93% and a selectivity of 94%.

(3) Removing step of the low-boiling point component

The bottom of an oldershow distilling column (10 plates, 40 mmφ) equipped with a vacuum jacket was supplied with the reaction mixture at a supplying rate of 600 g/hr, and only the upper layer of the distillate was refluxed at a pressure of 100 mmHg for distilling off the low-boiling point component (LB) and water which is generated in the reaction. The temperature of the bottom was 115° C., and the temperature of the distillate was 35° C.

(4) Recovering step of the catalyst from the high-boiling point component

Using a stainless steel flash-distiller (WFE, Wiped film evaporator, 100 mmφ×height 200 mm), the bottom product from the bottom of the distilling column was flash-distilled at a pressure of 40 mmHg and a distilling rate of 600 g/hr to remove the manganese salene complex as the catalyst and the high-boiling point component (HB) by-produced in the reaction, and the solution comprised of the reaction product KIP and the solvent DIBK as a distillate was distilled off. The temperature of the distillate was 98° C.

(5) Recovery of KIP and the recycling step of the solvent

The distillate was supplied to the thirteenth plate from the top of an oldershow distilling column equipped with a vacuum jacket (30 plates, 40 mmφ) at a supplying rate of 600 g/hr, and distilled at a pressure of 30 mmHg and a reflux ratio of 1.0 for separating KIP from DIBK for purification. 956 g of KIP was obtained by distilling KIP as a side-cut solution off from the 23th plate from the top. The distillate from the overhead was recycled to the oxidizing reactor and the bottom product was supplied to the flash-distilling column. The temperature of the bottom was 162° C., the temperature of the side-cut plate was 131° C., and the temperature of the distillate was 74° C. The separated solvent was analyzed by gas chromatography, and the impurities (cyclopentanone) and KIP were not detected.

The above operation was repeated 10 times, but the activity of the oxidizing catalyst in the oxidizing reaction was deteriorated very little (conversion: 95%, selectivity: 94%), and the high activity was kept.

Example 2

Except that the removal of the low-boiling point component in Example 1 was performed, this time, through the distilling operation with a distilling column (3a), the flash-distilling operation with a flash distiller (3b), and the dephlegmating operation with a dephlegmator (3c), ketoisophorone was obtained in the same manner as in Example 1.

The distilling operation (3a) was carried out in the same manner as in the separating step (3) of the low-boiling point component in Example 1. The flash-distilling operation (3b) was carried out by distilling, using a stainless flash-distiller (WFE, Wiped film evaporator, 100 mmφ×height 200 mm), the distillate from the overhead of the distilling column used in the distilling operation (3a) at 40° C. and a pressure of 60 mmHg. Further, the dephlegmating operation (3c) was conducted by dephlegmating the flash-distilled distillate at 40° C. and a pressure of 40 mmHg.

Hereinafter, the balance-of-material (weight %) in each operation is shown below.

(1) Isomerizing step

Composition of the supply solution: α-IP 100% by weight

Composition of the distillate: β-IP 97.0% by weight; α-isophorone 2.0% by weight; cyclopentanone 1.0% by weight.

(2) Oxidizing step

Composition of the supply solution: α-IP 0.5% by weight; β-IP 22.3% by weight; DIBK 75.76% by weight; DABCO 1.5% by weight; manganese salene complex: 0.04% by weight; cyclopentanone 0.2% by weight; water: 0.0% by weight Composition of the reaction mixture: α-isophorone 1.0% by weight; β-IP 0.4% by weight; ketoisophorone 22.0% by weight; DIBK 72.36% by weight; DABCO 1.5% by weight; manganese salene complex 0.04% by weight; cyclopentanone 0.2% by weight, water 2.5% by weight (3) Removing step of the low-boiling point component (3a) Distilling operation Composition of the supply solution: the same as the composition of the reaction mixture in the oxidizing step (2)

Composition of the distillate: α-isophorone 1.0% by weight; β-IP 0.4% by weight; ketoisophorone 22.0% by weight; DIBK 75.06% by weight; DABCO 1.5% by weight; manganese salene complex 0.04% by weight; cyclopentanone 0.0% by weight; water 0.0% by weight (3b) Flash-distilling operation Composition of the supply solution: the same as the composition of the reaction mixture in the oxidizing step (2)

Composition of the distillate: α-isophorone 1.0% by weight; β-IP 0.4% by weight; ketoisophorone 22.0% by weight; DIBK 75.05% by weight; DABCO 1.5% by weight; manganese salene complex 0.04% by weight; cyclopentanone 0.10% by weight; water 0.0% by weight (3c) Dephlegmating operation Composition of the supply solution: the same as the composition of the reaction mixture in the oxidizing step (2)

Composition of the solution to be dephlegmated: α-isophorone 1.0% by weight; β-IP 0.4% by weight; ketoisophorone 22.0% by weight; DIBK 74.88% by weight; DABCO 1.5% by weight; manganese salene complex: 0.04% by weight; cyclopentanone 0.18% by weight; water 0.0% by weight (4) Recovering step of the catalyst from the high-boiling point component Composition of the supply solution: the same as the composition of the distillate resulted from the distilling operation (3a) in the removing step (3) of the low-boiling point component Composition of the distillate: α-isophorone 1.0% by weight; β-IP 0.4% by weight; ketoisophorone 21.3% by weight; DIBK 75.80% by weight; DABCO 1.5% by weight; manganese salene complex 0.0% by weight; cyclopentanone 0.0% by weight; water 0.0% by weight.

(5) Recovery of KIP and recycling step of the solvent

Composition of the supply solution: the same as the composition of the distillate in the recovering step (4) of the solvent from the high-boiling point-component Composition of the distillate: α-isophorone 6.0% by weight; β-IP 0.0% by weight; ketoisophorone 94.0% by weight; DIBK 0.0% by weight; DABCO 0.0% by weight; manganese salene complex 0.0% by weight; cyclopentanone 0.0% by weight; water 0.0% by weight.

The above operation was repeated 10 times, but the activity of the oxidizing catalyst in the oxidizing reaction was deteriorated very little (conversion: 95%, selectivity: 94%), and the high activity of the oxidizing catalyst was maintained.

Comparative Example 1

Without undergoing the removing step (3) of the low-boiling point component, as in Example 1, the reaction mixture formed in the oxidizing step (2) was subjected to the recovering step (4) of the oxidizing catalyst and the recycling step (5) of recovering KIP and recycling the solvent. This operation was repeated seven times, and there was formed KIP with a conversion of 83% and a selectivity of 90%, and the catalytic activity was significantly deteriorated.

Example 3

Independently of the isomerizing reaction, a cycle of operations comprising (2) the oxidizing step, (3) the removing step of the low-boiling point component, (4) the recovering step of the catalyst from the high-boiling point component, and (5) the recycling step comprising the recovery of KIP and the recycling of the solvent in Example 1 was repeated ten times. The activity of the oxidizing catalyst in the oxidizing reaction was deteriorated very little (conversion: 95%, selectivity: 94%), and the high activity was maintained.

Comparative Example 2

In the recycling step (5) comprising the recovery of KIP and the recycling of the solvent, the reaction cl mixture was distilled at a reflux ratio of 0.5, and the separated solvent was analyzed by gas chromatography. 1,200 ppm of KIP was detected. The solvent recycled to the oxidizing reaction considerably deteriorated the activity of the oxidizing catalyst in the oxidizing reaction (conversion: 87%, selectivity: 90%).

What is claimed is:

1. A process for producing ketoisophorone comprising:

a step for oxidizing β-isophorone in an inert solvent in the presence of an oxidizing catalyst to form ketoisophorone;

a step for separating ketoisophorone and the solvent from the resultant reaction mixture; and a step of recycling at least the separated solvent to the oxidizing step;

wherein the oxidizing catalyst is a complex salt of a transition metal and an N,N'-disalicylidenediamine, the solvent from which a low-boiling point component having a boiling point of 100 to 180° C. as a by-product has been removed is recycled to the oxidizing step, and the low-boiling point component is a component that poisons the oxidizing catalyst.

2. A process according to claim 1, wherein the amount of the low-boiling point component contained in the solvent which is recycled to the oxidizing step is 0 to 5,000 ppm (weight basis).

3. A process according to claim 2, wherein the amount of the low-boiling point component contained in the solvent which is recycled to the oxidizing step is 0 to 1,000 ppm (weight basis).

4. A process according to claim 1, wherein the low-boiling point component is a non-conjugated cyclic ketone.

5. A process according to claim 1, wherein the low-boiling point component is a $C_{4-20}$ cycloalkanone.

6. A process according to claim 1, wherein the solvent which is recycled to the oxidizing step is substantially free from ketoisophorone.

7. A process according to claim 1, wherein a low-boiling point component having a boiling point of 120 to 140° C. and an inert solvent having a boiling point of 150 to 180° C. are separated from each other in the separating step, and the separated inert solvent is recycled to the oxidizing step.

8. A process according to claim 1, wherein the oxidizing catalyst is a complex represented by the following formula (1a) or (1b):

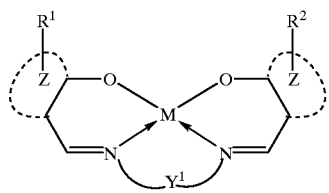

(1a)

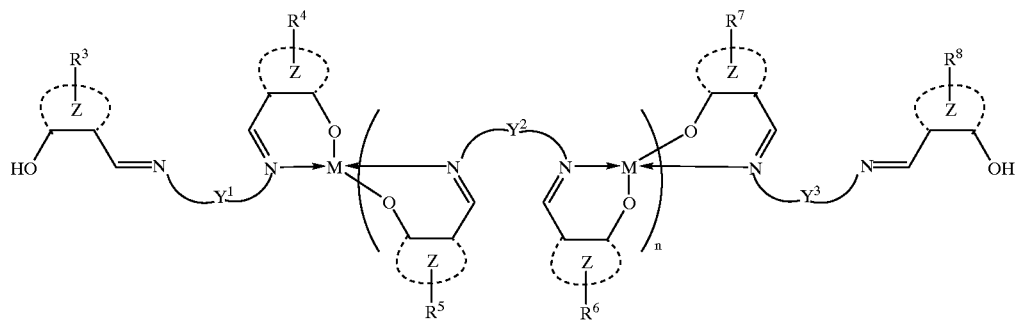

(1b)

wherein M represents vanadium (V), manganese (Mn), iron (Fe), cobalt (Co), or copper (Cu); $R^1$, $R^2$, $R^3$, $R^4$, $R^5$, $R^6$, $R^7$, and $R^8$ are the same or different, each representing a hydrogen atom, a halogen atom, an alkyl group, a hydroxyl group, an alkoxyl group, or a hydroxymethyl group; $Y^1$, $Y^2$, and $Y^3$ are the same or different, each representing an alkylene group, a cycloalkylene group, or an arylene group; each of the rings Z represents an aromatic ring; and n is an integer of 0 or 1 or larger.

9. A process according to claim 1, wherein a cyclic base is used as a co-catalyst in the oxidizing step.

10. A process according to claim 9, wherein the co-catalyst is an azabicyclo$C_{7-12}$alkane.

11. A process according to claim 1, wherein the separating step comprises:
a distilling step for removing the low-boiling point component from the reaction mixture;
a distilling step for separating the oxidizing catalyst from the reaction mixture; and
a distilling step for separating ketoisophorone and the inert solvent from the reaction mixture.

12. A process according to claim 1, wherein the separating step comprises: a distilling step for removing the low-boiling point component from an oxidation reaction mixture; a distilling step for separating the oxidizing catalyst from the reaction mixture from which the low-boiling point component has been removed; and a distilling step for separating ketoisophorone and the inert solvent from the reaction mixture from which the oxidizing catalyst has been removed.

13. A process according to claim 1, wherein α-isophorone is isomerized in the presence of an isomerizing catalyst to produce β-isophorone, and the produced β-isophorone is subjected to the oxidizing step.

14. A process according to claim 13, wherein the isomerizing catalyst is an aliphatic $C_{5-20}$ polycarboxylic acid.

15. A process for producing ketoisophorone comprising:
(1) a step for isomerizing β-isophorone in the presence of an isomerizing catalyst to form β-isophorone;
(2) a step for oxidizing the β-isophorone in an inert solvent in the presence of an oxidizing catalyst to form ketoisophorone;
(3) a step for individually separating a low-boiling point component having a boiling point of 100 to 180° C., the oxidizing catalyst, the solvent, and ketoisophorone from the oxidation reaction mixture; and
(4) a step of reusing the separated solvent as a solvent for the oxidizing reaction;
wherein the low-boiling point component includes a product produced upon decomposition of the isomerizing catalyst.

\* \* \* \* \*